(12) United States Patent
Aoshima et al.

(10) Patent No.: US 10,081,701 B2
(45) Date of Patent: Sep. 25, 2018

(54) COMPOSITION FOR MAGNETIC RECORDING MEDIUM AND MAGNETIC RECORDING MEDIUM

(71) Applicant: FUJIFILM Corporation, Minato-ku, Tokyo (JP)

(72) Inventors: Toshihide Aoshima, Minami-ashigara (JP); Kazutoshi Katayama, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 507 days.

(21) Appl. No.: 14/472,663

(22) Filed: Aug. 29, 2014

(65) Prior Publication Data
US 2015/0064500 A1 Mar. 5, 2015

(30) Foreign Application Priority Data

Aug. 30, 2013 (JP) .................. 2013-179046
Aug. 29, 2014 (JP) .................. 2014-175643

(51) Int. Cl.
| | | |
|---|---|---|
| *C08G 18/32* | (2006.01) | |
| *C08G 18/76* | (2006.01) | |
| *C08G 18/80* | (2006.01) | |
| *C08G 18/75* | (2006.01) | |
| *C08G 18/72* | (2006.01) | |
| *G11B 5/702* | (2006.01) | |
| *C07C 271/40* | (2006.01) | |
| *C07C 271/42* | (2006.01) | |
| *C07C 271/56* | (2006.01) | |
| *C07C 271/58* | (2006.01) | |

(52) U.S. Cl.
CPC ........ *C08G 18/3215* (2013.01); *C07C 271/40* (2013.01); *C07C 271/42* (2013.01); *C07C 271/56* (2013.01); *C07C 271/58* (2013.01); *C08G 18/724* (2013.01); *C08G 18/755* (2013.01); *C08G 18/757* (2013.01); *C08G 18/7621* (2013.01); *C08G 18/7642* (2013.01); *C08G 18/8016* (2013.01); *C08G 18/8019* (2013.01); *C08G 18/8025* (2013.01); *C08G 18/8029* (2013.01); *G11B 5/7021* (2013.01)

(58) Field of Classification Search
CPC ........... C08G 18/3215; C08G 18/7642; C08G 18/8025; C08G 18/8019; C08G 18/8016; C08G 18/8029; C08G 18/7621; C08G 18/757; C08G 18/724; C08G 18/755; G11B 5/7021; C07C 271/42; C07C 271/56; C07C 271/58

See application file for complete search history.

(56) References Cited

U.S. PATENT DOCUMENTS

| | | | | |
|---|---|---|---|---|
| 2,621,168 A | * | 12/1952 | Ross ................ | C08G 63/68 528/279 |
| 3,037,946 A | * | 6/1962 | Barnes .............. | C08G 18/4879 521/131 |
| 3,063,964 A | * | 11/1962 | Khawam .......... | C08G 18/3215 521/176 |
| 4,868,060 A | | 9/1989 | Ryoke et al. | |
| 5,030,481 A | | 7/1991 | Hashimoto et al. | |
| 6,245,877 B1 | * | 6/2001 | Rodriguez ........ | C08G 18/12 525/504 |
| 8,674,017 B2 | | 3/2014 | Ooga et al. | |
| 2006/0024515 A1 | | 2/2006 | Murayama et al. | |
| 2011/0272183 A1 | | 11/2011 | Ooga et al. | |
| 2016/0039967 A1 | * | 2/2016 | Rukavina .......... | C08G 18/72 428/174 |
| 2016/0122460 A1 | * | 5/2016 | Fedurco ............ | C08G 18/677 428/626 |

FOREIGN PATENT DOCUMENTS

| | | | |
|---|---|---|---|
| EP | 2383118 A2 | * | 11/2011 |
| JP | 62-003420 A | | 1/1987 |
| JP | 62-241128 A | | 10/1987 |
| JP | 62-298921 A | | 12/1987 |
| JP | 03-003117 A | | 1/1991 |
| JP | 2004-145933 A | | 5/2004 |
| JP | 2006-040472 A | | 2/2006 |
| WO | 2010/084872 A1 | | 7/2010 |
| WO | WO 2014/173838 A1 | * | 10/2014 |

OTHER PUBLICATIONS

Office Action dated Aug. 25, 2015 from the Japanese Patent Office in counterpart Japanese Application No. 2014-175643.
Office Action dated Oct. 6, 2017 from the U.S. Patent and Trademark Office in copending U.S. Appl. No. 15/685,202.
Office Action dated May 9, 2018, issued by the United States Patent and Trademark Office in co-pending U.S. Appl. No. 15/685,202.

* cited by examiner

*Primary Examiner* — Rabon Sergent
(74) *Attorney, Agent, or Firm* — Sughrue Mion, PLLC

(57) ABSTRACT

An aspect of the present invention relates to a composition, which is a composition for a magnetic recording medium and comprises an isocyanate compound in the form of an adduct of a polyhydroxyl compound having one or more aromatic carbon rings and three or more hydroxyl groups per molecule with a polyisocyanate having two or more isocyanate groups per molecule.

11 Claims, No Drawings

COMPOSITION FOR MAGNETIC RECORDING MEDIUM AND MAGNETIC RECORDING MEDIUM

CROSS-REFERENCE TO RELATED APPLICATIONS

This application claims priority under 35 U.S.C 119 to Japanese Patent Application No. 2013-179046 filed on Aug. 30, 2013 and Japanese Patent Application No. 2014-175643 filed on Aug. 29, 2014. Each of the above applications is hereby expressly incorporated by reference, in its entirety.

BACKGROUND OF THE INVENTION

Field of the Invention

The present invention relates to a composition for a magnetic recording medium and to a magnetic recording medium. More particularly, it relates to a composition for magnetic recording medium that can provide a magnetic recording medium having both high surface smoothness and running durability, and to a magnetic recording medium having a coating formed of the above composition.

Discussion of the Background

Curing agents are widely employed in particulate magnetic recording media (for example, see Japanese Unexamined Patent Publication (KOKAI) Showa No. 62-3420, Japanese Unexamined Patent Publication (KOKAI) Showa No. 62-241128 or English language family member U.S. Pat. No. 4,868,060, Japanese Unexamined Patent Publication (KOKAI) Showa No. 62-298921, which are expressly incorporated herein by reference in their entirety) to enhance the running durability of magnetic recording media by imparting good heat resistance and abrasion resistance to coatings such as magnetic layers and nonmagnetic layers.

SUMMARY OF THE INVENTION

In addition to running durability, high surface smoothness is also required for magnetic recording media. To enhance surface smoothness, it is effective to increase the dispersion of the ferromagnetic powder contained in the magnetic layer and the nonmagnetic powder located in the layer beneath the magnetic layer. However, conventional curing agents sometimes compromise dispersibility. In particular, this tendency is seen in magnetic layers containing ferromagnetic powder in which the particle size has been reduced to achieve higher density recording.

As set forth above, it has conventionally been difficult to achieve both high surface smoothness and running durability.

An aspect of the present invention provides for a magnetic recording medium having both high surface smoothness and running durability.

The present inventors conducted extensive research. This resulted in the discovery that an isocyanate compound, in the form of an adduct of a polyhydroxyl compound having one or more aromatic carbon rings and three or more hydroxyl groups per molecule with a polyisocyanate having two or more isocyanate groups per molecule, was a curing agent that permitted the formation of a high-strength coating without compromising the dispersibility of the powder. The present inventors presumed that this was due to the fact that urethane bonds, formed by the reaction of the hydroxyl groups contained in the polyhydroxyl compound and the isocyanates contained in the polyisocyanate in the isocyanate compound, could contribute to enhancing the coating strength, and that the aromatic carbon rings derived from the polyhydroxyl compound could contribute to the dispersion of the powder, particularly to maintaining dispersion of fine particles of ferromagnetic powder.

The present invention was devised on the basis of the above knowledge.

An aspect of the present invention relates to a composition, which is a composition for a magnetic recording medium and comprises an isocyanate compound in the form of an adduct of a polyhydroxyl compound having one or more aromatic carbon rings and three or more hydroxyl groups per molecule with a polyisocyanate having two or more isocyanate groups per molecule.

In an embodiment, the polyhydroxyl compound comprises one or more aromatic carbon rings onto which a hydroxyl group has been directly substituted.

In an embodiment, the polyhydroxyl compound comprises two or more aromatic carbon rings per molecule.

In an embodiment, the polyhydroxyl compound comprises two or more aromatic carbon groups per molecule, with the aromatic carbon rings being connected by a connecting group.

In an embodiment, the aromatic carbon ring comprised in the polyhydroxyl compound is a benzene ring.

In an embodiment, the cyclic structure comprised in the polyhydroxyl compound is only one or more aromatic carbon rings.

In an embodiment, the average molecular weight of the isocyanate compound ranges from 500 to 15,000 as a weight average molecular weight of a dibutylamine adduct of the isocyanate compound that has been dibutylaminated with dibutylamine.

In an embodiment, the polyhydroxyl compound is selected from the group consisting of a compound denoted by formula (1) and a compound denoted by formula (2):

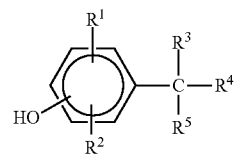

(1)

wherein, in formula (1), each of $R^3$, $R^4$, and $R^5$ independently denotes a hydrogen atom, methyl group, or a substituent selected from the group consisting of the following substituents:

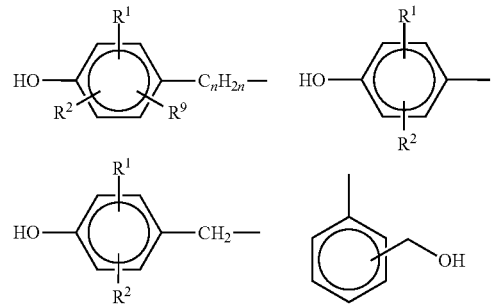

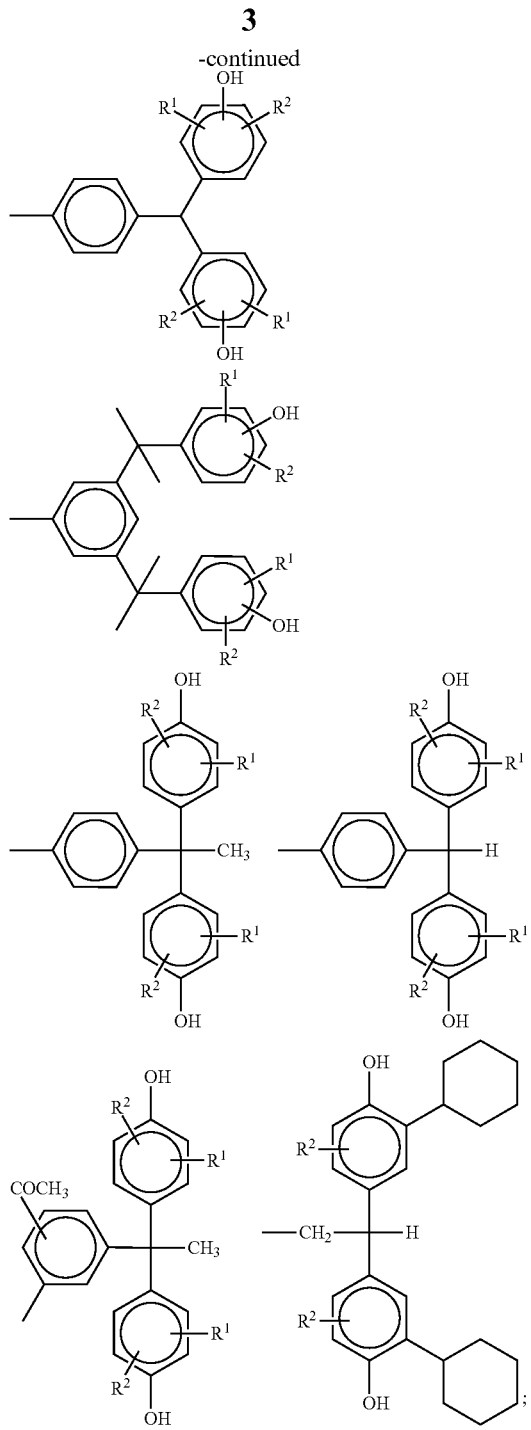

each of $R^1$, $R^2$, and $R^9$ independently denotes a hydrogen atom, methyl group, or cyclohexyl group; and n denotes an integer ranging from 0 to 2;

(2)

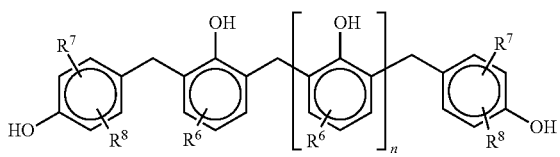

wherein, in formula (2), $R^6$ denotes a hydrogen atom, methyl group, phenyl group, or cyclohexyl group; each of $R^7$ and $R^8$ independently denotes a hydrogen atom, methyl group, or cyclohexyl group; and m denotes 0 or 1.

In an embodiment, the isocyanate compound is a reaction product of the polyhydroxyl compound and the polyisocyanate, with the number of moles of the polyisocyanate being 0.8 to 1.5-fold a number of moles of hydroxyl groups comprised in the polyhydroxyl compound.

In an embodiment, the number of isocyanate groups comprised per molecule of the polyisocyanate is two.

In an embodiment, the above composition further comprises binder.

In an embodiment, the polyisocyanate comprises isophorone diisocyanate, and the cyclic structure comprised in the polyhydroxyl compound is only one or more aromatic carbon rings.

In an embodiment, the above composition further comprises binder and ferromagnetic powder.

In an embodiment, the average particle size of the ferromagnetic powder ranges from 10 nm to 50 nm.

A further aspect of the present invention relates to a magnetic recording medium, which comprises a magnetic layer on a nonmagnetic support, and the magnetic layer is a layer formed by heating the above composition.

An aspect of the present invention can provide a magnetic recording medium having good running durability in addition to exhibiting good electromagnetic characteristics due to having high surface smoothness.

Other exemplary embodiments and advantages of the present invention may be ascertained by reviewing the present disclosure.

DETAILED DESCRIPTION OF THE EMBODIMENTS

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The following preferred specific embodiments are, therefore, to be construed as merely illustrative, and non-limiting to the remainder of the disclosure in any way whatsoever. In this regard, no attempt is made to show structural details of the present invention in more detail than is necessary for fundamental understanding of the present invention; the description making apparent to those skilled in the art how several forms of the present invention may be embodied in practice.

Composition for Magnetic Recording Medium

An aspect of the present invention relates to a composition, which is a composition for a magnetic recording medium and comprises an isocyanate compound in the form of an adduct of a polyhydroxyl compound having one or more aromatic carbon rings and three or more hydroxyl groups per molecule with a polyisocyanate having two or more isocyanate groups per molecule. The composition for a magnetic recording medium is also referred to as the "magnetic recording medium-use composition" or simply as the "composition", hereinafter. In the magnetic recording medium-use composition of an aspect of the present invention, the isocyanate compound functions as a curing agent forming a crosslinked structure (in a curing reaction) with the binder that is employed as a structural component of coatings such as a magnetic layer and a nonmagnetic layer during the manufacturing of a magnetic recording medium, and the magnetic recording medium-use composition can be employed as a curing agent composition.

The magnetic recording medium-use composition will be described in greater detail below. In the present invention, unless specifically stated otherwise, the groups that are described can be substituted or unsubstituted. When a given group comprises one or more substituents, examples of the substituent are an alkyl group (such as an alkyl group with 1 to 6 carbon atoms), a hydroxyl group, an alkoxy group (such as an alkoxy group with 1 to 6 carbon atoms), a halogen atom (such as a fluorine atom, chlorine atom, or bromine atom), a cyano group, an amino group, a nitro group, an acyl group, and a carboxyl group. With regard to a group having one or more substituents, the number of carbon atoms means the number of carbon atoms of the portion excluding the substituent. In the present invention, the word "to" indicates a range including the preceding and succeeding numbers as the minimum and maximum values thereof.

Polyhydroxyl Compound

The polyhydroxyl compound has one or more aromatic carbon rings and three or more hydroxyl groups per molecule. By having three or more hydroxyl groups per molecule, the adduct that is obtained by reaction with the polyisocyanate can be an isocyanate compound having multiple urethane bonds per molecule. This is also thought to contribute to the formation of a high-strength coating. When taking into account solubility in solvent, the number of hydroxyl groups that is contained in the polyisocyanate compound is desirably 3 to 5, preferably 3 or 4. Among the hydroxyl groups contained per molecule, at least one hydroxyl group is desirably substituted directly onto the aromatic carbon ring without a connecting group. That is, so-called phenolic hydroxyl groups are desirable. It is preferable for all of the hydroxyl groups to be directly substituted onto the aromatic carbon ring.

The polyhydroxyl group contains one or more aromatic carbon ring per molecule in addition to the hydroxyl groups. The isocyanate compound that is obtained from the polyhydroxyl compound contains one or more aromatic carbon ring, which is thought to contribute to maintaining good dispersion of the powder in the magnetic recording medium.

The aromatic carbon ring can be monocyclic or polycyclic in structure. A polycyclic ring can be in the form of a condensed ring or ring assembly in which two or more rings are connected by a single bond or a connecting group. The connecting groups can be alkylene groups such as alkylene groups having 1 to 3 carbon atoms; specific examples are methylene groups optionally substituted with methyl groups or the like, and optionally substituted ethylene groups.

Examples of the above aromatic carbon rings are benzene rings, naphthalene rings, biphenyl rings, anthracene rings, pyrene rings, phenanthrene rings, condensed rings of one or more of the above with an aliphatic ring, and ring assemblies in which two or more of these rings structures are connected. Ring assemblies in which a benzene ring is connected to another benzene ring by a connecting group are desirable.

The polyhydroxyl compound can contain an aliphatic carbon ring, heterocycle, or some other cyclic structure with one or more aromatic carbon rings. The other cyclic structure is desirably an aliphatic carbon ring and preferably a cyclohexane ring. From the perspective of further enhancing dispersion and coating strength, the cyclic structures that are contained in the above polyhydroxyl compound are desirably only aromatic carbon rings. The number of aromatic carbon rings contained per molecule is one or more, as stated above, desirably two or more, and preferably, three or more. By way of example, this number is three or more but five or less.

Examples of desirable embodiment of the polyhydroxyl compound set forth above are the compound denoted by the following formula (1) and the compound denoted by the following formula (2):

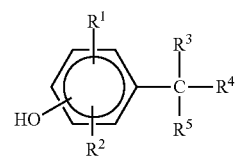

In formula (1), each of $R^3$, $R^4$, and $R^5$ independently denotes a hydrogen atom, a methyl group, or a substituent selected from the group consisting of the following substituents:

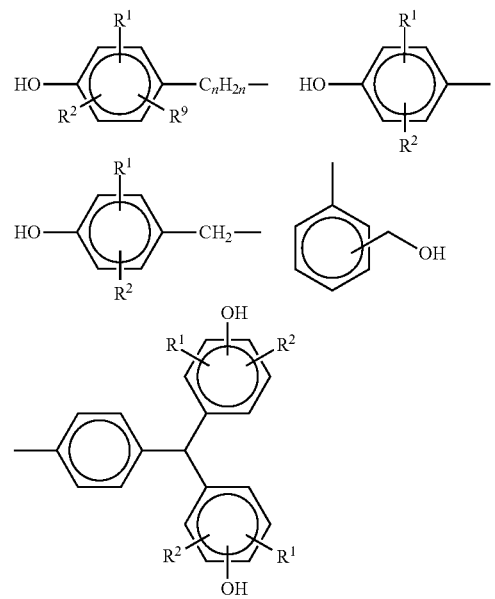

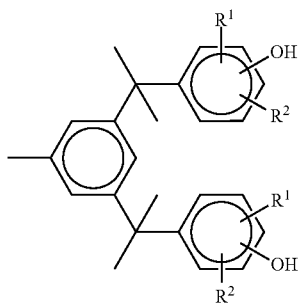

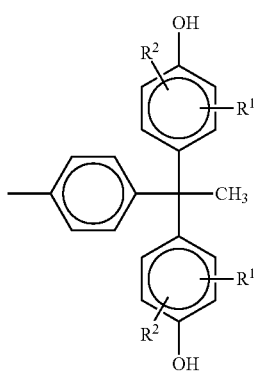

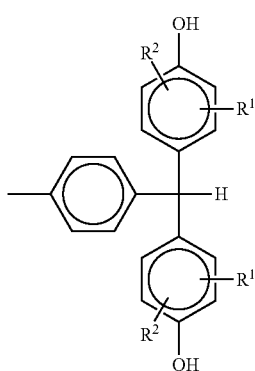

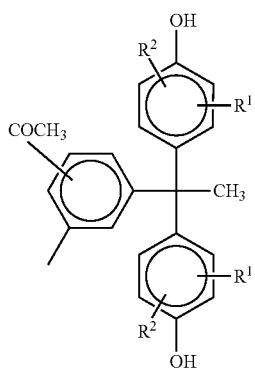

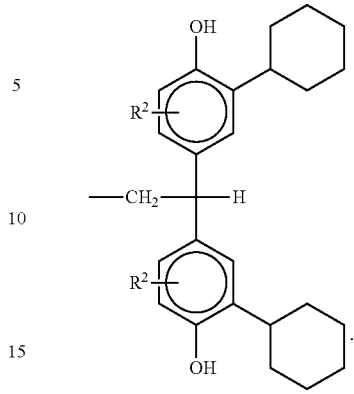

Each of $R^1$, $R^2$, and $R^9$ independently denotes a hydrogen atom, methyl group, or cyclohexyl group.

n denotes an integer ranging from 0 to 2.

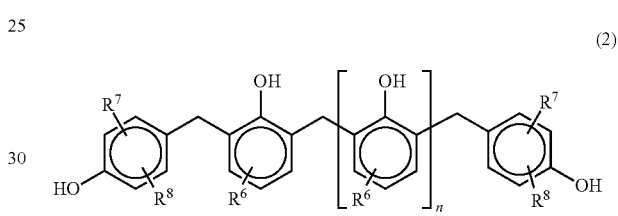

(2)

In formula (2), $R^6$ denotes a hydrogen atom, methyl group, phenyl group, or cyclohexyl group.

Each of $R^7$ and $R^8$ independently denotes a hydrogen atom, methyl group, or cyclohexyl group. m denotes 0 or 1.

The inorganicity/organicity value (denoted as "I/O") is known to be an index indicating the properties of an organic compound. The I/O value of a compound can be obtained based on the detailed description of the I/O value given in *Organic Conceptual Diagrams—Foundations and Applications* (by Yoshio Koda, Sankyo Publishing (Ltd.), 1984). The I/O value of the above polyhydroxyl compound desirably falls within a range of 0.3 to 2.7, preferably within a range of 0.3 to 1.5, and more preferably, within a range of 0.3 to 1.0. The organicity of the I/O value depends primarily on the number of carbon atoms in an organic compound, with one carbon atom counting as 20. The inorganicity depends primarily on the substituents of an organic compound, with a single hydroxyl group being 100, and is determined based on how the group affects the boiling point of the compound. The I/O value of a phenol is 1.0. The polyhydroxyl compound having an I/O value falling within the range set forth above can be said to have a hydrocarbon ratio that is the same as or greater than that of a phenol. The adduct (isocyanate compound) that is obtained from such a polyhydroxyl compound is highly hydrophobic and highly compatible with binders. Thus, it is presumed to contribute to powder dispersion, particularly to maintaining the dispersion of fine particles of ferromagnetic powder.

The following compounds are specific examples of the polyhydroxyl compound set forth above:

P-1
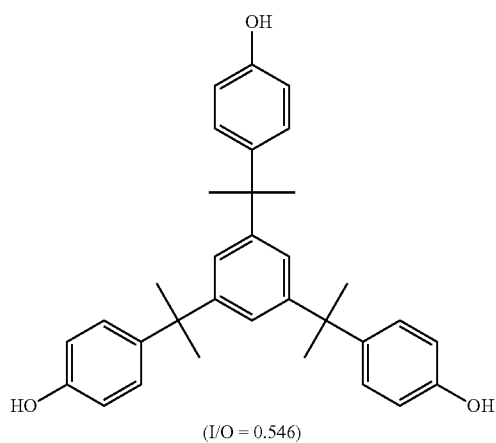
(I/O = 0.546)
P-2
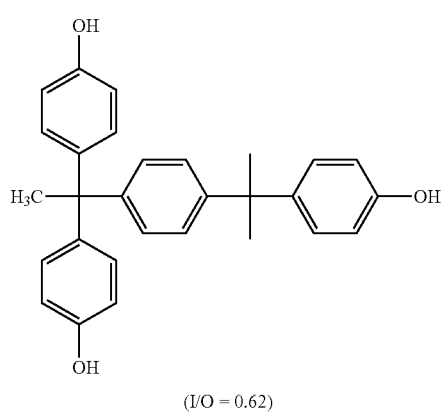
(I/O = 0.62)
P-3
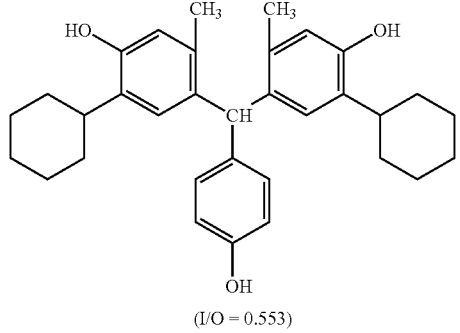
(I/O = 0.553)
P-4
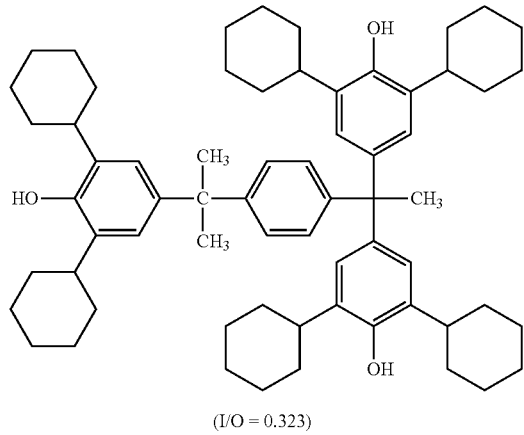
(I/O = 0.323)
-continued
P-5
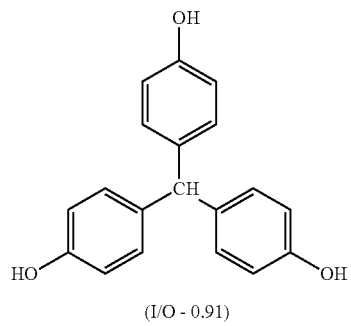
(I/O - 0.91)
P-6
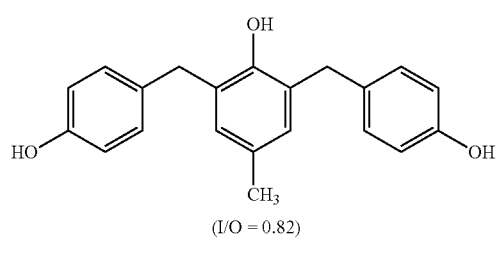
(I/O = 0.82)
P-7
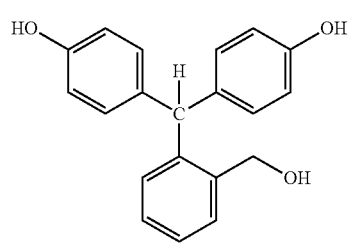
(I/O = 0.86)
P-8
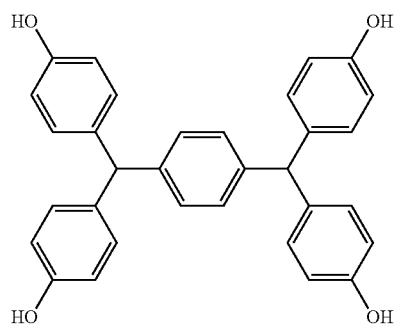
(I/O = 0.74)
P-9
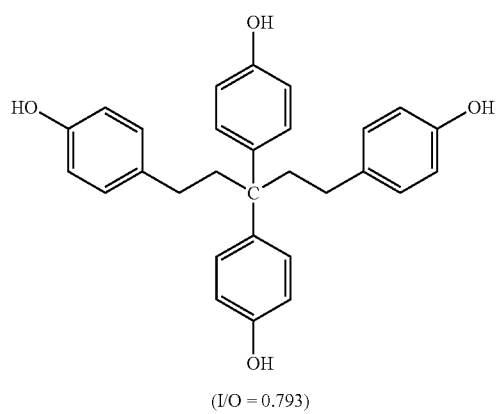
(I/O = 0.793)

P-10
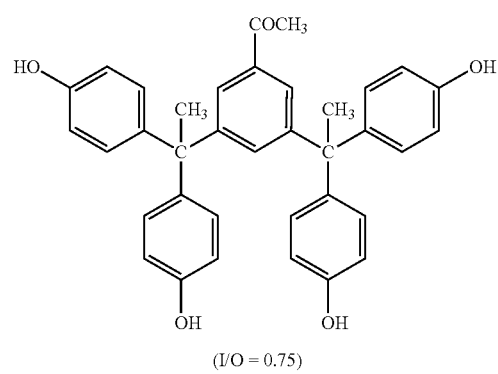
(I/O = 0.75)
P-11
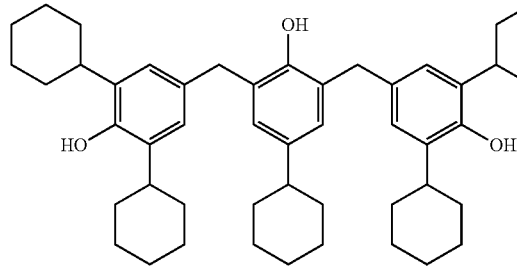
(I/O = 0.395)
P-12
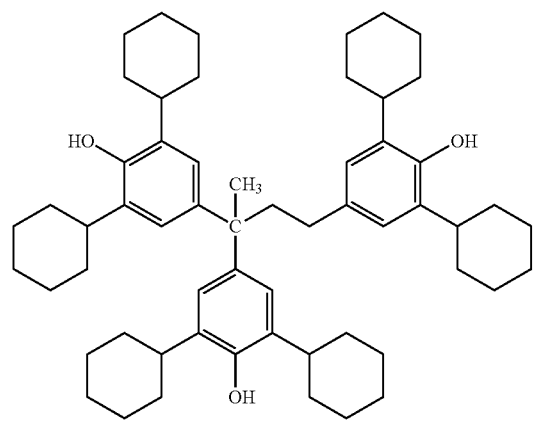
(I/O = 0.351)
P-13
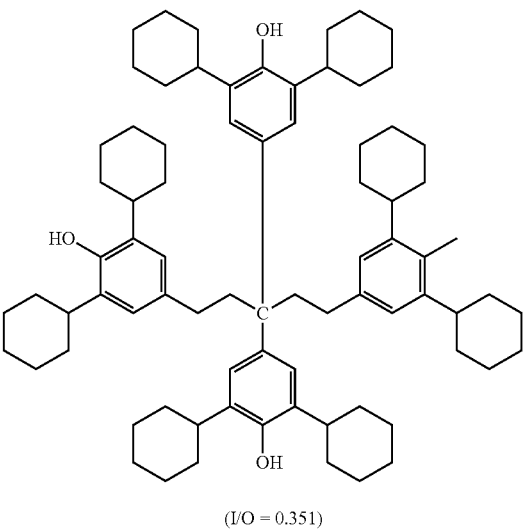
(I/O = 0.351)
P-14
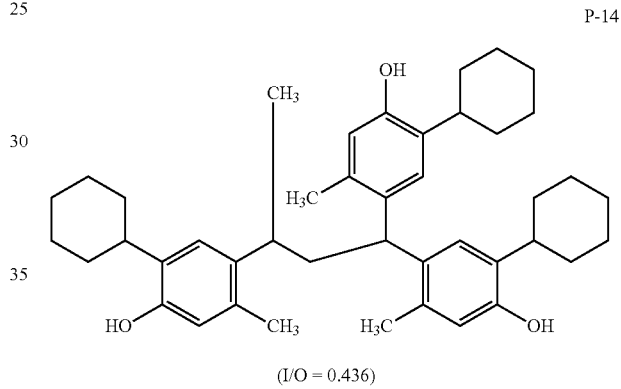
(I/O = 0.436)
P-15
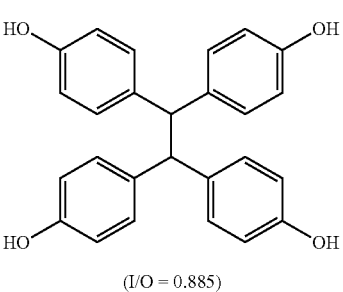
(I/O = 0.885)
P-16
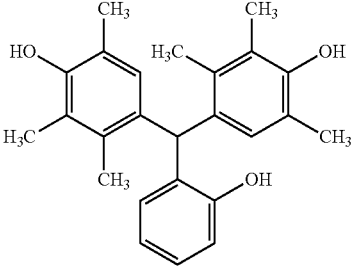
(I/O = 0.669)

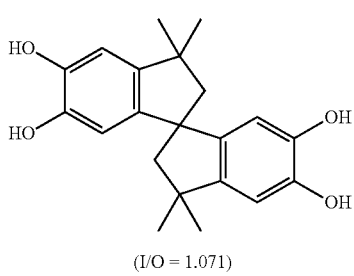

P-17

(I/O = 1.071)

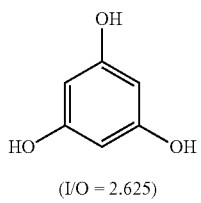

P-18

(I/O = 2.625)

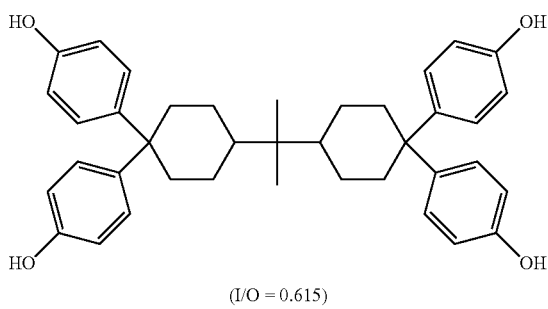

P-19

(I/O = 0.615)

Of the above compounds, compounds P-1, P-2, P-5, P-8, P-10, P-14, and P-16 are desirable.

Polyisocyanate

Known compounds can be employed as the polyisocyanate having two or more isocyanate groups per molecule that forms an adduct by reacting with the above polyhydroxyl compound; a bifunctional isocyanate having two isocyanate groups is preferred. Examples are aromatic isocyanate compounds and aliphatic isocyanate compounds. Polyisocyanates that have intramolecular cyclic structures such as aromatic rings and aliphatic rings are desirable. Specific examples of the cyclic structures that are contained are benzene groups and cyclohexane groups.

Specific examples of the polyisocyanate are isophorone diisocyanate, m-phenylene diisocyanate, p-phenylene diisocyanate, 2,6-tolylene diisocyanate, 2,4-tolylene diisocyanate, naphthalene-1,4-diisocyanate, diphenylmethane-4,4'-diisocyanate, 3,3'-dimethoxybiphenyl diisocyanate, 3,3'-dimethyldiphenylmethane-4,4'-diisocyanate, xylylene-1,4-diisocyanate, xylylene-1,3-diisocyanate, 4-chloroxylylene-1,3-diisocyanate, 2-methylxylylene-1,3-diisocyanate, 4,4'-diphenylpropane diisocyanate, 4,4'-diphenylhexafluoropropane diisocyanate, trimethylene diisocyanate, hexamethylene diisocyanate, propylene-1,2-diisocyanate, butylene-1,2-diisocyanate, cyclohexylene-1,2-diisocyanate, cyclohexylene-1,3-diisocyanate, cyclohexylene-1,4-diisocyanate, dicyclohexylmethane-4,4'-diisocyanate, 1,4-bis(isocyanatemethyl)cyclohexane, and 1,3-bis(isocyanatemethyl)cyclohexane. Of these, isophorone diisocyanate, 2,4-tolylene diisocyanate, 2,6-tolylene diisocyanate, xylylene-1,4-diisocyanate, and xylylene-1,3-diisocyanate are desirable. Using these compounds as primary starting materials, compounds rendered multifunctional as adducts (addition products) with polyols, such as trimers thereof (biurets or isocyanurates) and trimethylol propanes; formaline condensates of benzene isocyanates; and the like are desirable. Among these, isophorone diisocyanate, 2,4-tolylene diisocyanate, 2,6-tolylene diisocyanate, xylylene-1,4-diisocyanate, and xylylene-1,3-diisocyanate are desirable.

Each of the above polyhydroxyl compounds and polyisocyanates can be synthesized by known methods or is available as a commercial product.

Isocyanate Compound

The magnetic recording medium-use composition of an aspect of the present invention contains an isocyanate compound in the form of an adduct of the above polyhydroxyl compound and polyisocyanate. In combining the above polyhydroxyl compound and polyisocyanate, a polyisocyanate that is bifunctional as set forth above is desirable; and isophorone diisocyanate, 2,4-tolylene diisocyanate, 2,6-tolylene diisocyanate, xylylene-1,4-diisocyanate, and xylylene-1,3-diisocyanate are preferred. A polyhydroxyl compound in the form of a compound denoted by formula (1) or (2) above is desirable, and a compound denoted by formula (1) is preferred. Of these, a combination of a compound denoted by formula (1) and isophorone diisocyanate is desirable.

Method of Synthesizing the Isocyanate Compound

The above adduct can be obtained, for example, by heating (at a heating temperature of 50° C. to 100° C., for example) the polyhydroxyl compound and the polyisocyanate in an organic solvent while stirring, or by heating at a relatively low temperature (such as 40° C. to 70° C., for example) while adding a catalyst such as stannous octoate. Examples of the organic solvent are ethyl acetate, chloroform, tetrahydrofuran, methyl ethyl ketone, acetone, acetonitrile, and toluene. The more hydroxyl groups contained in the polyhydroxyl compound that react with isocyanate groups in the polyisocyanate, the larger the number of urethane bonds that will be contained in the adduct, which is desirable from the perspective of enhancing coating strength. From this viewpoint, the number of moles (number of molecules) of polyisocyanate that are reacted with the polyhydroxyl compound is desirably 0.-fold 8 to 1.5-fold the number of moles (number of molecules) of hydroxyl groups (hydroxyl group equivalent) contained in the polyhydroxyl compound.

The weight average molecular weight (polystyrene converted value) of the dibutylamine adduct that has been obtained by ditubutylaminating with dibutylamine all of the isocyanate groups contained in the isocyanate can be employed as an index of the molecular weight of the isocyanate. The molecular weight of the isocyanate compound, as the number average molecular weight of the above dibutylamine adduct, desirably falls within a range of 500 to 15,000, preferably within a range of 1,000 to 10,000. Such an isocyanate compound of relatively high molecular weight is desirable to contribute to further enhancing the coating strength.

The magnetic recording medium-use composition of an aspect of the present invention contains the isocyanate compound set forth above. Various other components that are commonly employed as components of magnetic recording media can also be incorporated. Examples of such components are binder, ferromagnetic powder, nonmagnetic powder, solvent, and additives. The details thereof are set forth further below.

Magnetic Recording Medium

A further aspect of the present invention relates to a magnetic recording medium comprising, on a nonmagnetic support, a magnetic layer containing ferromagnetic powder and binder. The magnetic recording medium has a magnetic layer that is formed by heating a magnetic recording medium-use composition containing ferromagnetic powder, binder, and the isocyanate compound set forth above. The fact that the isocyanate compound can serve as a curing agent and form a crosslinked structure with binder when heated can contribute to enhancing the coating strength of the magnetic layer, thereby making it possible to provide a magnetic recording medium having good running durability. However, as set forth above, it was difficult to both enhance coating strength and maintain powder dispersion with conventional curing agents. By contrast, based on an aspect of the present invention, use of the above isocyanate compound makes it possible to enhance coating strength while maintaining powder dispersion. An aspect of the present invention thus devised can provide a magnetic recording medium having good running durability while having high surface smoothness with good ferromagnetic powder dispersion.

Ferromagnetic Powder

As set forth above, the isocyanate compound is a component making it possible to enhance the coating strength without greatly decreasing the dispersibility of the powder. Thus, it can be used as a curing agent in magnetic recording media for high density recording in which fine particles of ferromagnetic powder are contained in a magnetic layer. For this reason, ferromagnetic powder with an average particle size of equal to or less than 50 nm is desirably employed. Ferromagnetic powder with an average particle size of equal to or less than 50 nm is magnetic powder that permits the high density recording that has been demanded in recent years. From the perspective of achieving higher density recording, the average particle size of the ferromagnetic powder is preferably equal to or less than 40 nm, more preferably equal to or less than 30 nm. From the perspective of magnetization stability, the average particle size is desirably equal to or greater than 10 nm, preferably equal to or greater than 15 nm.

The average particle size of the ferromagnetic powder is a value that is measured by the following method with a transmission electron microscope.

Ferromagnetic powder is photographed at a magnification of 100,000-fold with a transmission electron microscope, and the photograph is printed on print paper at a total magnification of 500,000-fold to obtain a photograph of the particles constituting the ferromagnetic powder. A target particle is selected from the photograph of particles that has been obtained, the contour of the particle is traced with a digitizer, and the size of the (primary) particle is measured. The term "primary particle" refers to an unaggregated, independent particle.

The above measurement is conducted on 500 randomly extracted particles. The arithmetic average of the particle size of the 500 particles obtained in this manner is adopted as the average particle size of the ferromagnetic powder. A Model H-9000 transmission electron microscope made by Hitachi can be employed as the above transmission electron microscope, for example. The particle size can be measured with known image analysis software, such as KS-400 image analysis software from Carl Zeiss.

In the present invention, the average particle size of the powder is the average particle size as obtained by the above method. The average particle size indicated in Examples further below was obtained using a Model H-9000 transmission electron microscope made by Hitachi and KS-400 image analysis software made by Carl Zeiss.

The method described in paragraph 0015 of Japanese Unexamined Patent Publication (KOKAI) No. 2011-048878, which is expressly incorporated herein by reference in its entirety, for example, can be employed as the method of collecting sample powder such as ferromagnetic powder from a magnetic layer for particle size measurement.

In the present invention, the size of the particles constituting powder such as ferromagnetic powder (referred to as the "particle size", hereinafter) is denoted as follows based on the shape of the particles observed in the above particle photograph:

(1) When acicular, spindle-shaped, or columnar (with the height being greater than the maximum diameter of the bottom surface) in shape, the particle size is denoted as the length of the major axis constituting the particle, that is, the major axis length.

(2) When platelike or columnar (with the thickness or height being smaller than the maximum diameter of the plate surface or bottom surface) in shape, the particle size is denoted as the maximum diameter of the plate surface or bottom surface.

(3) When spherical, polyhedral, of unspecific shape, or the like, and the major axis constituting the particle cannot be specified from the shape, the particle size is denoted as the diameter of an equivalent circle. The term "diameter of an equivalent circle" means that obtained by the circle projection method.

The "average acicular ratio" of a powder refers to the arithmetic average of values obtained for the above 500 particles by measuring the length of the minor axis, that is the minor axis length, of the particles measured above, and calculating the value of the (major axis length/minor axis length) of each particle. The term "minor axis length" refers to, in the case of the particle size definition of (1), the length of the minor axis constituting the particle; in the case of (2), the thickness or height, and in the case of (3), since the major axis and minor axis cannot be distinguished, (major axis length/minor axis length) is deemed to be 1 for the sake of convenience.

When the particle has a specific shape, such as in the particle size definition of (1) above, the average particle size is the average major axis length. In the case of (2), the average particle size is the average plate diameter, with the average plate ratio being the arithmetic average of (maximum diameter/thickness or height). For the definition of (3), the average particle size is the average diameter (also called the average particle diameter).

Hexagonal ferrite powder is a specific example of desirable ferromagnetic powder. From the perspectives of achieving higher density recording and magnetization stability, the average particle size (average plate diameter) of hexagonal ferrite powder desirably ranges from 10 nm to 50 nm, preferably 20 nm to 50 nm. Reference can be made to Japanese Unexamined Patent Publication (KOKAI) No. 2011-216149, which is expressly incorporated herein by reference in its entirety, paragraphs 0134 to 0136, for details on hexagonal ferrite powder.

Ferromagnetic metal powder is also a specific example of desirable ferromagnetic powder. From the perspectives of achieving higher density recording and magnetization stability, the average particle size (average major axis length) of ferromagnetic metal powder desirably ranges from 10 nm to 50 nm, preferably 20 nm to 50 nm. Reference can be made to Japanese Unexamined Patent Publication (KOKAI) No. 2011-216149, paragraphs 0137 to 0141, for details on ferromagnetic metal powder.

Binder

A single resin or a mixture of multiple resins in the form of polyurethane resin, polyester resin, polyamide resin, vinyl chloride resin, styrene, acrylonitrile, methyl methacrylate, and other copolymerized acrylic resins; nitrocellulose and other cellulose resins; and epoxy resin, phenoxy resin, polyvinyl acetal, polyvinyl butyral, and other polyvinyl alkyral resins can be used as the binder. Of these, polyurethane resin, acrylic resin, cellulose resin, and vinyl chloride resin are desirable. These resins can also be employed as binders in the nonmagnetic layer, described further below. From the perspective of getting the crosslinking reaction between the binder and the isocyanate compound to proceed smoothly, the incorporation of a functional group having an active hydrogen, such as a hydroxyl group, is desirable. The content of the active hydrogen-containing functional group falls within a range of 0.1 meq/g to 2 meq/g. For the above binder, reference can be made to Japanese Unexamined Patent Publication (KOKAI) No. 2010-24113, which is expressly incorporated herein by reference in its entirety, paragraphs 0028 to 0031. The curing agent can be added for use in a quantity of 10 weight parts to 80 weight parts per 100 weight parts of binder, for example, and is desirably added in a quantity of 50 weight parts to 80 weight parts from the perspective of further enhancing the coating strength. Binder can be used in the magnetic layer, and in the nonmagnetic layer, described further below, within a range of 5 weight parts to 50 weight parts, for example, and desirably 10 weight parts to 30 weight parts, per 100 weight parts of ferromagnetic powder or nonmagnetic powder.

Additives can be added as needed to the magnetic layer. Examples of additives are abrasives, lubricating agents, dispersing agents and adjuvants, antifungal agents, antistatic agents, oxidation-inhibiting agents, and carbon black. The additives can be used by suitably selecting commercial products based on the properties desired.

Nonmagnetic Layer

Details of the nonmagnetic layer will be described next. In the magnetic recording medium of an aspect of the present invention, a nonmagnetic layer containing nonmagnetic powder and binder can be present between the nonmagnetic support and the magnetic layer. The nonmagnetic powder that is employed in the nonmagnetic layer can be an organic or inorganic material. Carbon black and the like can also be employed. Examples of inorganic materials are metals, metal oxides, metal carbonates, metal sulfates, metal nitrides, metal carbides, and metal sulfides. These nonmagnetic powders are available as commercial products and can be manufactured by known methods. For details, reference can be made to Japanese Unexamined Patent Publication (KOKAI) No. 2011-216149, paragraphs 0146 to 0150.

The binders, lubricants, dispersing agents, additives, solvents, dispersing methods, and the like that are employed in the magnetic layer can be applied to the nonmagnetic layer. In particular, known techniques relating to the magnetic layer in terms of quantities and types of binder and quantities and types of additives can be applied. Carbon black, organic powders, and the like can be added to the nonmagnetic layer. In this regard, reference can be made, for example, to Japanese Unexamined Patent Publication (KOKAI) No. 2010-24113, paragraphs 0040 to 0042.

The magnetic recording medium-use composition of an aspect of the present invention can also be used to form the nonmagnetic layer. Since the isocyanate compound contained in the composition can maintain the dispersibility of powder, it can contribute to forming a nonmagnetic layer having high surface smoothness in which nonmagnetic powder is well dispersed. Increasing the surface smoothness of the nonmagnetic layer that is positioned beneath the magnetic layer, in addition to that of the magnetic layer, is an effective way to increase the surface smoothness of the magnetic recording medium. The particle size of the nonmagnetic powder, as a crystallite size, desirably falls within a range of 4 nm to 500 nm, preferably within a range of 40 nm to 100 nm. The average particle size of the nonmagnetic powder desirably falls within a range of 5 nm to 500 nm, preferably within a range of 10 nm to 200 nm.

Nonmagnetic Support

Known nonmagnetic supports such as biaxially stretched polyethylene terephthalate, polyethylene naphthalate, polyamide, polyamide-imide, and aromatic polyamide, are examples of nonmagnetic supports. Of these, polyethylene terephthalate, polyethylene naphthalate, and polyamide are desirable.

These supports can be subjected in advance to a corona discharge, plasma treatment, adhesion-enhancing treatment, heat treatment, or the like. The surface roughness of nonmagnetic supports that can be employed in the present invention is desirably a centerline average roughness Ra of 3 nm to 10 nm at a cutoff value of 0.25 mm.

Layer Structure

In the thickness structure of the magnetic recording medium of an aspect of the present invention, the thickness of the nonmagnetic support is desirably 3 μm to 80 μm. The thickness of the magnetic layer can be optimized based on the saturation magnetization level of the magnetic head employed, the length of the head gap, and the bandwidth of the recording signal. It is generally 10 nm to 150 nm, desirably 20 nm to 120 nm, and preferably, 30 nm to 100 nm. The magnetic layer can comprise at least a single layer, or be separated into two or more magnetic layers having different magnetic characteristics. Structures relating to known multilayered magnetic layers can be applied.

The thickness of the nonmagnetic layer is, for example, 0.1 μm to 3.0 μm, desirably 0.1 μm to 2.0 μm, and preferably, 0.1 μm to 1.5 μm. The nonmagnetic layer in the present invention includes an essentially nonmagnetic layer containing trace quantities of ferromagnetic powder, for example, either as impurities or intentionally, in addition to the nonmagnetic powder. The essentially nonmagnetic layer means a layer exhibiting a residual magnetic flux density of equal to or less than 10 mT, a coercive force of equal to or less than 7.96 kA/m (100 Oe), or a residual magnetic flux density of equal to or less than 10 mT and a coercive force of equal to or less than 7.96 kA/m (100 Oe). The nonmagnetic desirably has no residual magnetic flux density or coercive force.

Backcoat Layer

A backcoat layer can be provided on the opposite side of the nonmagnetic support from that on which the magnetic layer is present. The backcoat layer desirably contains carbon black and inorganic powder. The formulations of the magnetic layer, nonmagnetic layer, and the like can be applied to the binder and various additives for forming the backcoat layer. The thickness of the backcoat layer is desirably equal to or less than 0.9 μm, preferably 0.1 μm to 0.7 μm. The above isocyanate compound can also be applied as the curing agent of the backcoat layer. Employing the above isocyanate compound as a curing agent makes it possible to form a backcoat layer of high coating strength in which the carbon black is well dispersed.

Manufacturing Process

The magnetic recording medium-use composition of an aspect of the present invention can be employed as is as the coating liquid (magnetic coating material) for forming the magnetic layer, or solvents, additives, and the like can be optionally added thereto for use.

The process of manufacturing the coating liquid for forming the magnetic layer, nonmagnetic layer, or backcoat layer normally comprises at least a kneading step, dispersing step, and mixing steps provided as needed before and after these steps. Each of these steps can be divided into two or more steps. All of the starting materials of the ferromagnetic powder, nonmagnetic powder, binder, carbon black, abrasive, antistatic agent, lubricant, solvent, and the like that are employed can be added at the start or part way through any of the steps. An individual starting material can also be divided up and added in two or more steps. For example, polyurethane can be divided up and added during a kneading step, dispersing step, and blending step for adjusting the viscosity following dispersion. Some of the steps of conventionally known manufacturing techniques can be employed. In the kneading step, an open kneader, continuous kneader, pressure kneader, extruder, or the like with powerful kneading force is desirably employed. Details on the kneading processing are given in Japanese Unexamined Patent Publications (KOKAI) Heisei Nos. 1-106338 and 1-79274, which are expressly incorporated herein by reference in their entirety. Glass beads or some other form of beads can be employed to disperse the magnetic layer coating liquid, nonmagnetic layer coating liquid, or backcoat layer coating liquid. Examples of such suitable dispersion media are high specific gravity dispersion media in the form of zirconia beads, titania beads, and steel beads. The particle diameters and fill rates of the dispersion media can be optimized for use. A known dispersion apparatus can be employed.

In the method for manufacturing a magnetic recording medium, for example, a magnetic layer can be formed by coating the magnetic layer coating liquid to a prescribed thickness on the surface of a running nonmagnetic support. Here, multiple magnetic layer coating liquids can be multilayer coated sequentially or simultaneously, or the nonmagnetic layer coating liquid and the magnetic layer coating liquid can be sequentially or simultaneously multilayer coated.

Following the coating step, the magnetic recording medium can be subjected to various post-processing, such as a drying treatment, an orientation treatment of a magnetic layer, and a surface smoothing treatment (calendering treatment). The heat treatment (thermal curing treatment) of the magnetic layer coating liquid can be conducted in any steps following the coating step, and a crosslinked structure can also be formed by heating in the drying treatment, calendering treatment, or the like. The drying treatment is desirably conducted such that the drying position of the coating is controlled by controlling the temperature and flow rate of the drying air and the coating rate. The coating rate is desirably 20 m/minute to 1,000 m/minute, and the temperature of the drying air is desirably equal to or higher than 60° C. A suitable degree of predrying can be conducted before entering the magnet zone for orientation processing. Calendering treatment conditions of a calendering roll temperature, for example, falling within a range of 60° C. to 100° C., desirably 70° C. to 100° C., preferably 80° C. to 100° C. can be employed. The pressure of the calender rolls, for example, falls within a range of 100 kg/cm to 500 kg/cm (approximately 98 kN/m to 490 kN/m), desirably within a range of 200 kg/cm to 450 kg/cm (approximately 196 kN/m to 441 kN/m), and preferably, within a range of 300 kg/cm to 400 kg/cm (approximately 294 kN/m to 392 kN/m). To enhance the smoothness of the magnetic layer surface, the surface of the nonmagnetic layer can be calendered. The calendering treatment of the nonmagnetic layer is desirably conducted under conditions set forth above.

The magnetic recording medium obtained following the calendering step can be thermally treated to conduct heat curing. The thermal treatment conditions can be suitably determined based on the blending formulation of the magnetic layer coating liquid. The heating temperature, for example, can be 35° C. to 100° C., desirably 50° C. to 80° C. The thermal treatment period can be, for example, 12 hours to 72 hours, desirably 24 hours to 48 hours.

The magnetic recording medium that is obtained can be cut to desired size for use by employing cutters, stampers, and the like. For details about methods of manufacturing magnetic recording media, reference can be made, for example, to Japanese Unexamined Patent Publication (KOKAI) No. 2010-24113, paragraphs 0051 to 0057.

An aspect of the present invention permits the formation of a magnetic layer of high surface smoothness in which ferromagnetic powder is well dispersed. For example, it can achieve a high surface smoothness in the form of a centerline average surface roughness Ra as measured by the method described in Examples further below that falls within a range of 1 nm to 6 nm, even one that falls within a range of 1 nm to 5 nm. Thus, according to an aspect of the present invention, it is possible to provide a magnetic recording medium for high density recording that affords good electromagnetic characteristics. The magnetic recording medium having a magnetic layer formed using the above isocyanate compound as a curing agent can also afford high running durability.

EXAMPLES

The present invention will be described in detail below based on Examples. However, the present invention is not limited to embodiments shown in Examples. The term "parts" given in Examples is weight parts unless otherwise stated.

The molecular weight of the polymer compounds set forth below is the weight average molecular weight (Mw), and the ratio of repeating units is a molar ratio.

Synthesis Examples of Isocyanate Compounds (NCO-1 to 10)

Synthesis Example 1: Synthesis of NCO-1

To an ethyl acetate suspension (470.7 g) of 355.6 g (1.60 mol) of isophorone diisocyanate (IPDI) and 169.6 g (0.40 mol) of polyhydroxyl compound (P-2) was added dropwise over an hour with stirring a solution of 471 mg of stannous octoate (Stanocto, made by Yoshitomi Seiyaku (Ltd.)) dissolved in 10 g of ethyl acetate. Following the dropwise addition, stirring was continued for 2 hours, after which stirring was conducted for 3 hours at 50° C. This yielded a solution (50 weight percent concentration) of an adduct of the polyhydroxyl compound and the polyisocyanate in the form of isocyanate compound (NCO-1).

The compound obtained was identified by FT-IR (KBr). The data are given below.

FT-IR (KBr) 3416 cm$^{-1}$, 2956 cm$^{-1}$, 2262 cm$^{-1}$, 1738 cm$^{-1}$, 1499 cm$^{-1}$, 1364 cm$^{-1}$, 1307 cm$^{-1}$, 1211 cm$^{-1}$, 1014 cm$^{-1}$, 853 cm$^{-1}$, 576 cm$^{-1}$.

Synthesis Examples 2 to 10:
Synthesis of NCO-2 to 10

In Synthesis Example 1, with the exceptions that P-2 was changed to the compounds given in Table 1 below and the polyisocyanates indicated in Table 1 were employed in the proportions indicated in Table 1, solutions of isocyanate compounds (NCO-2 to 10) were obtained in the same manner as in Synthesis Example 1.

NCO-5 that was obtained was identified by FT-IR (KBr). The data are given below.

FT-IR (KBr) 3418 cm$^{-1}$, 2955 cm$^{-1}$, 2263 cm$^{-1}$, 1734 cm$^{-1}$, 1519 cm$^{-1}$, 1477 cm$^{-1}$, 1364 cm$^{-1}$, 1305 cm$^{-1}$, 1195 cm$^{-1}$, 1069 cm$^{-1}$, 997 cm$^{-1}$, 761 cm$^{-1}$, 578 cm$^{-1}$.

Synthesis Examples 11 to 13:
Synthesis of NCO-11 to 13

In Synthesis Example 1, with the exceptions that the polyhydroxyl compound was changed to the compounds indicated in Table 1 and the polyisocyanates indicated in Table 1 were employed in the proportions indicated in Table 1, solutions of isocyanate compounds (NCO-11 to 13) were obtained in the same manner as in Synthesis Example 1.

Example 1

(1) Preparation of Magnetic Layer Coating Liquid Containing Ferromagnetic Hexagonal Ferrite Powder
Ferromagnetic platelike hexagonal ferrite powder: 100 parts
    Composition excluding oxygen (molar ratio): Ba/Fe/Co/Zn=1/9/0.2/1
    Hc: 160 kA/m (approximately 2,000 Oe)
    Average plate diameter: 20 nm
    Average plate ratio: 2.7
    BET specific surface area: 60 m$^2$/g
    σs: 46 A·m$^2$/kg (approximately 46 emu/g)
Polyurethane resin: 5 parts
    (Vylon (Japanese registered trademark) UR4800, made by Toyobo Co., Ltd.
    functional group: SO$_3$Na, functional group concentration: 70 eq/t)
Vinyl chloride resin: 10 parts
    (MR104 made by Kaneka Co., Ltd., hydroxyl group concentration: 0.33 meq/g)
α-Al$_2$O$_3$ (particle size: 0.1 μm): 8 parts
Carbon black (average particle diameter: 20 nm): 0.5 part
Cyclohexanone: 110 parts The above components were kneaded in an open kneader and then dispersed in a sand mill. The following components were admixed to the solution obtained and the mixture was ultrasonically treated. The mixture was then filtered with a filter having an average pore diameter of 1 μm to prepare a magnetic layer coating liquid.
Butyl stearate: 2 parts
Stearic acid: 0.5 part
Methyl ethyl ketone: 50 parts
Cyclohexanone: 50 parts
Toluene: 3 parts
Isocyanate compound NCO-1: 5 parts (2) Preparation of Nonmagnetic Layer Coating Liquid
Nonmagnetic powder (α-Fe$_2$O$_3$ hematite): 80 parts
    Major axis length: 0.15 μm
    BET specific surface area: 52 m$^2$/g
    pH: 6
    Tap density: 0.8
    DBP oil absorption capacity: 27 to 38 g/100 g
    Surface treatment agents: Al$_2$O$_3$, SiO$_2$
Carbon black: 20 parts
    Average primary particle diameter: 0.020 μm
    DBP oil absorption capacity: 80 mL/100 g
    pH: 8.0
    BET specific surface area: 250 m$^2$/g
    Volatile content: 1.5 percent
Polyurethane resin: 19 parts
    Branched side chain-containing polyester polyol/diphenylmethane diisocyanate
    —SO$_3$Na=100 eq/ton
Methyl ethyl ketone: 150 parts
Cyclohexanone: 150 parts The various components of the above coating material were kneaded in an open kneader and then dispersed in a sand mill. The following components were admixed to the solution obtained and the mixture was filtered with a filter having an average pore diameter of 1 μm to prepare a coating liquid for an undercoating layer (nonmagnetic layer).
Butyl stearate: 1.5 parts
Stearic acid: 1 part
Methyl ethyl ketone: 50 parts
Cyclohexanone: 50 parts
Toluene: 3 parts
Polyisocyanate compound (Coronate 3041, made by Nippon Polyurethane Industry Co., Ltd.): 5 parts (3) Preparation of Backcoat Layer Coating Liquid
Carbon black (average particle diameter 40 nm): 85 parts
Carbon black (average particle diameter 100 nm): 3 parts
Nitrocellulose: 28 parts
Polyurethane resin: 58 parts
Copper phthalocyanine dispersing agent: 2.5 parts
Nipporan 2301 (made by Nippon Polyurethane Industry Co., Ltd.): 0.5 part
Methyl isobutyl ketone: 0.3 part
Methyl ethyl ketone: 860 parts
Toluene: 240 parts The above components were prekneaded in a roll mill and then dispersed in a sand mill. Four parts of polyester resin (Vylon 500, made by Toyobo Co., Ltd.), 14 parts of polyisocyanate compound (Coronate 3041, made by Nippon Polyurethane Industry Co. Ltd.), and 5 parts of α-Al$_2$O$_3$ (made by Sumitomo Chemical Co., Ltd.) were added. The mixture was stirred and filtered to prepare a backcoat layer coating liquid.

Simultaneous multilayer coating of the above nonmagnetic layer coating liquid in a quantity calculated to yield a dry thickness of 1.0 μm, immediately followed by the magnetic layer coating liquid thereover in a quantity calculated to yield a dry magnetic layer thickness of 0.1 μm was conducted on a polyethylene naphthalate resin support 5 μm in thickness with a centerline surface roughness of the magnetic layer coating surface of 0.001 μm and a base surface that had been rendered hydrophilic by a preliminary corona treatment. While the two layers were still wet, orientation and drying were conducted with a cobalt magnet having a 0.5 T (approximately 5000 G) magnetic force and a solenoid having a 0.4 T (approximately 4,000 G) magnetic force. Subsequently, the backcoat coating liquid was applied to the base surface that had been subjected to the preliminary corona treatment in a quantity calculated to yield a dry thickness of 0.5 μm. Processing was then conducted with a seven-stage calender comprised of metal rolls at a temperature of 100° C. at a rate of 80 m/min, and the product was slit to ½ inch width to prepare the magnetic tape of Example 1.

Examples 2 to 10, Comparative Examples 1 to 7

With the exception that the isocyanate compound employed in Example 1 was changed to those given in Tables 1 and 2, the magnetic tapes of Examples 2 to 10 and Comparative Examples 1 to 7 were prepared in the same manner as in Example 1.

A 0.3 g quantity of each of the isocyanate compounds employed in the magnetic layer in Examples and Comparative Examples was mixed with a 4 mL THF (tetrahydrofuran) solution of dibutylamine adjusted to 0.4 M. The mixtures were left standing for 1 hour and the weight average molecular weight (polystyrene converted value) of the dibutylamine adduct obtained was measured. The measurement values are given in Tables 1 and 2 below.

[Measurement Methods]

<Average Surface Roughness of the Tape>

An atomic force microscope (AFM: Nanoscope III made by Digital Instrument) was employed in contact mode to measure a 40 μm×40 μm area on the magnetic layer surface and the centerline average surface roughness (Ra) was measured.

<Electromagnetic Characteristics: SN Ratio (Signal-to-Noise Ratio)>

An LTO (Linear-Tape-Open)-Gen4 (Generation 4) drive was employed to record signals with linear recording densities of 172 kfci and 86 kfci with a recording track of 11.5 jam and a reproduction track width of 5.3 μm. The reproduction signals were frequency analyzed with a spectral analyzer. The ratio of the carrier signal output during 172 kfci signal recording to the integrated noise of the entire spectral bandwidth during 86 kfci signal recording was adopted as the SN ratio. An LTO-Gen4 tape made by FUJIFILM was employed as a reference tape. Adopting the S/N ratio of the reference tape as 0 dB, the relative S/N ratio values of the various tapes were calculated. A S/N ratio of equal to or higher than 0 dB was determined to indicate good electromagnetic characteristics as a magnetic recording medium for high density recording.

<Amount of Grime on the Tape Surface>

The tape was run at an angle of 150 degrees to, and such that the surface of the magnetic layer was brought into contact with, the edge of a square bar having a cross-section of 7 mm×7 mm made of $Al_2O_3$/TiC, a 100 m length was slid in one pass under conditions of a load of 100 g and a speed of 6 m/s, the edge portion of the square bar was observed under a microscope, and the state of adhesion of grime was evaluated. The evaluation was organoleptic on a scale of 1 to 10, with 10 indicating little grime and 1 indicating maximum grime.

The grime evaluated by the above method was primarily generated by shaving of the magnetic layer surface. The lower the level of the evaluation result, the poorer the shave running durability of the surface of the magnetic layer. An evaluation level of equal to or higher than 8 could indicate little grime (shaving of the magnetic layer surface) and permitted a determination of good running durability.

The results of the above are given in Tables 1 and 2 below.

TABLE 1

| | Isocyanate compound | Starting materials of isocyanate compound | | Number of moles of polyisocyanate relative to number of moles of hydroxyl groups comprised in the polyhydroxyl compound | Mw of dibutyl-amine adduct | Surface rough-ness Ra (nm) | S/N (dB) | Running durability Amount of grime (Poor) 1-10 (Good) |
| --- | --- | --- | --- | --- | --- | --- | --- | --- |
| | | Polyhydroxyl compound | Polyisocyanate | | | | | |
| Example 1 | NCO-1 | P-2 See below | See below | 1.33 | 5600 | 4.6 | 1.0 | 8 |
| Example 2 | NCO-2 | P-16 See below | See below | 1.33 | 2600 | 4.6 | 1.0 | 10 |
| Example 3 | NCO-3 | P-8 See below | See below | 1.33 | 6800 | 4.7 | 1.0 | 9 |
| Example 4 | NCO-4 | P-14 See below | See below | 1.33 | 12100 | 4.2 | 1.0 | 7 |
| Example 5 | NCO-5 | See below | See below | 1.25 | 1200 | 4.2 | 1.0 | 7 |
| Example 6 | NCO-6 | See below | See below | 1.33 | 1400 | 4.2 | 1.0 | 7 |
| Example 7 | NCO-7 | P-2 See below | See below | 1.33 | 6000 | 4.2 | 1.0 | 7 |
| Example 8 | NCO-8 | P-2 See below | See below | 1.33 | 7200 | 4.2 | 1.0 | 7 |
| Example 9 | NCO-9 | P-2 See below | See below | 1.33 | 5400 | 4.1 | 1.0 | 6 |
| Example 10 | NCO-10 | P-2 See below | Trimethylol propane/ m-xylylene disocyanate = ⅓ adduct | 1.33 | 10200 | 4 | 1.0 | 6 |
| Comp. Ex. 1 | NCO-11 | See below | See below | 1.5 | 600 | 4.3 | 0.5 | 4 |

TABLE 1-continued
| Comp. Ex. 2 | NCO-12 | See below | See below | 1.5 | 600 | 4.5 | 0.5 | 4 |
| Comp. Ex. 3 | NCO-13 | See below | See below | 1.5 | 600 | 4.2 | 0.5 | 4 |
Polyhydroxyl compounds in Table 1 above
Examples 1, 7, 8, 9 and 10
P-2
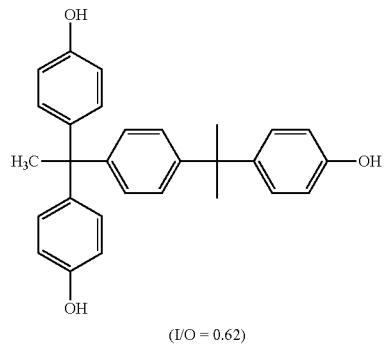
(I/O = 0.62)
Example 2
P-16
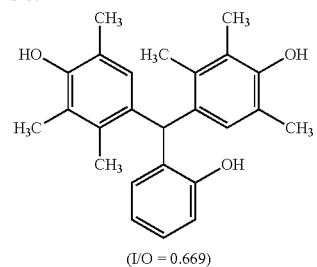
(I/O = 0.669)
Example 3
P-8
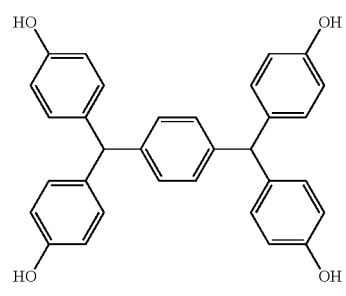
(I/O = 0.74)
Example 4
P-14
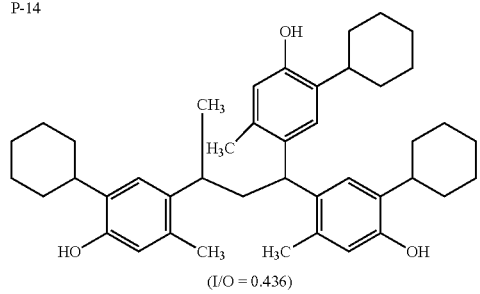
(I/O = 0.436)
Example 5
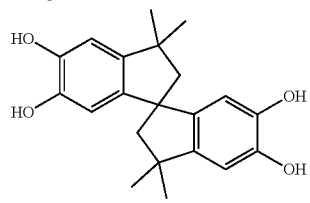

TABLE 1-continued

Example 6

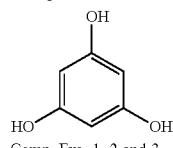

Comp. Exs. 1, 2 and 3

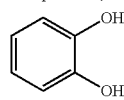

Polyisocyanate compounds in Table 1 above

Examples 1-6, Comp. Ex. 1

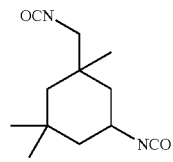

Example 7, Comp. Ex. 2

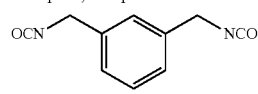

Example 9

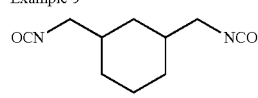

Example 8, Comp. Ex. 3

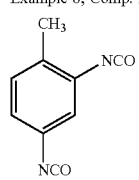

TABLE 2

| | Isocyanate compound | Mw of dibutylamine adduct | Surface roughness Ra (nm) | S/N(dB) | Running durability Amount of grime (Poor)1-10(Good) |
|---|---|---|---|---|---|
| Comp. Ex. 4 | Trimethylol propane/ m-xylylene diisocyanate =1/3 adduct | 2000 | 4.0 | 0.0 | 4 |
| Comp. Ex. 5 | Trimethylol propane/ isophorone diisocyanate =1/3 adduct | 2200 | 4.3 | 0.0 | 4 |
| Comp. Ex. 6 | Trimethylol propane/ tolylene diisocyanate =1/3 adduct | 2100 | 4.1 | 0.0 | 4 |
| Comp. Ex. 7 | | 500 | 4.7 | −0.5 | 3 |
| Comp. Ex. 8 | | 286 | 5.0 | −0.5 | 2 |

Evaluation Results

Based on the results given in Table 1, the magnetic tapes of Examples were determined to have both high surface smoothness and good running durability. Among them, particularly good results were obtained in Examples 1 to 3, in which a magnetic layer curing agent in the form of an isocyanate compound was employed that was obtained using a polyisocyanate in the form of isophorone diisocyanate and a polyhydroxyl compound having a cyclic structure in the form of only multiple aromatic carbon rings.

By contrast, the magnetic tapes of Comparative Examples 1 to 3 exhibited poor running durability, in which a magnetic layer curing agent in the form of an isocyanate compound was employed that was obtained using a polyhydroxyl compound in the form of a dihydroxyl compound.

In addition, it was not possible to achieve both surface smoothness and running durability in the magnetic tapes of Comparative Examples 4 to 8, in which curing agents in the form of conventionally employed isocyanate compounds were employed in the magnetic layer.

Among Comparative Examples, some had surface smoothness equivalent to that of the Examples but poor S/N ratios. This was thought to have been caused by deterioration of the S/N ratio because of diminished orientation of the ferromagnetic powder in the magnetic layer caused by decreased dispersion of the ferromagnetic powder.

Based on the above results, an aspect of the present invention could be determined to provide a magnetic recording medium that had both high surface smoothness and good running durability, and afforded good electromagnetic characteristics.

The magnetic recording medium of an aspect of the present invention is useful as a backup tape or the like that is required to afford highly reliable use over an extended period.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any Examples thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A composition, which is a composition for a magnetic recording medium and comprises an isocyanate compound in the form of an adduct of a polyhydroxyl compound having three or more aromatic carbon rings and three or more hydroxyl groups per molecule with one or more polyisocyanate(s) selected from the group consisting of m-phenylene diisocyanate, p-phenylene diisocyanate, 2,6-tolylene diisocyanate, naphthalene-1,4-diisocyanate, diphenylmethane-4,4'-diisocyanate, 3,3'-dimethoxybiphenyl diisocyanate, 3,3'-dimethyldiphenylmethane-4,4'-diisocyanate, xylylene-1,4-diisocyanate, 4-chloroxylylene-1,3-diisocyanate, 2-methylxylylene-1,3-diisocyanate, 4,4'-diphenylpropane diisocyanate, 4,4'-diphenylhexafluoropropane diisocyanate, trimethylene diisocyanate, hexamethylene diisocyanate, propylene-1,2-diisocyanate, butylene-1,2-diisocyanate, cyclohexylene-1,2-diisocyanate, cyclohexylene-1,3-diisocyanate, cyclohexylene-1,4-diisocyanate, dicyclohexylmethane-4,4'-diisocyanate, and 1,4-bis(isocyanatemethyl) cyclohexane, wherein the polyhydroxyl compound is selected from the group consisting of a compound denoted by formula (1) and a compound denoted by formula (2):

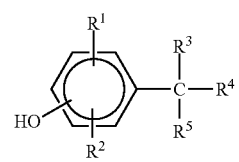

(1)

wherein, in formula (1), each of $R^3$, $R^4$, and $R^5$ independently denotes a hydrogen atom, a methyl group, or a substituent selected from the group consisting of the following substituents:

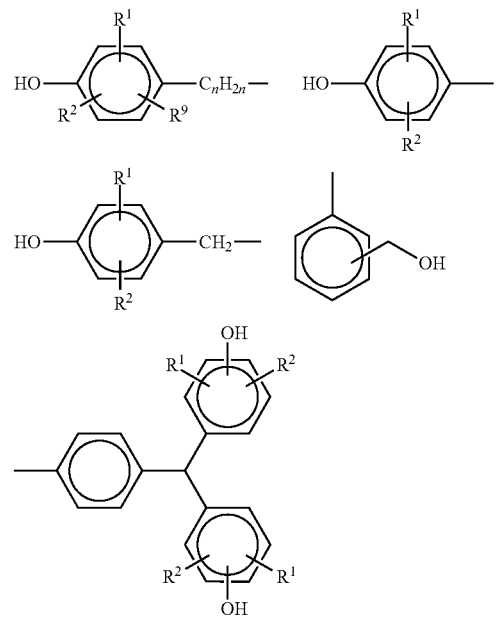

-continued

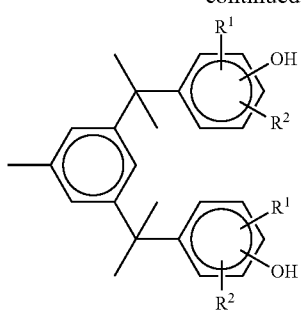

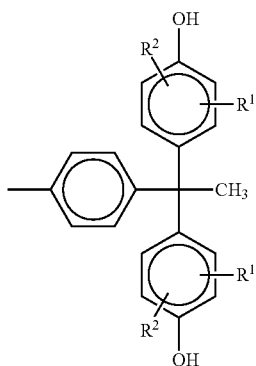

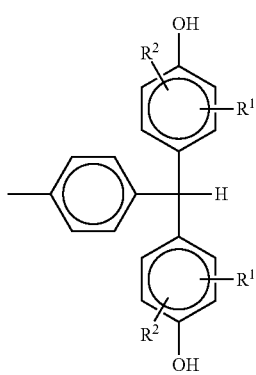

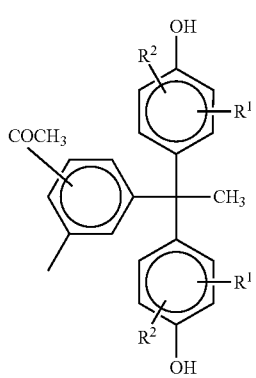

-continued

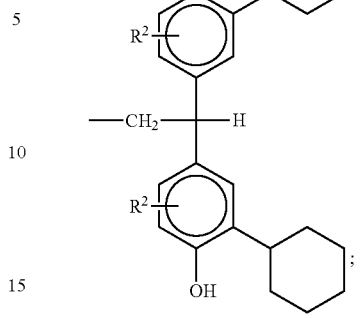

each of $R^1$, $R^2$, and $R^9$ independently denotes a hydrogen atom, a methyl group, or a cyclohexyl group; and n denotes an integer ranging from 0 to 2;

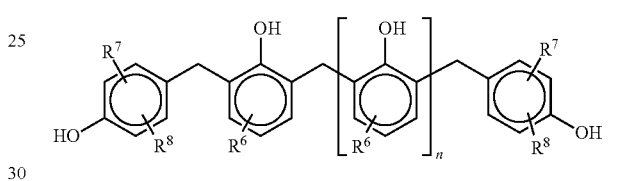

wherein, in formula (2), $R^6$ denotes a hydrogen atom, a methyl group, a phenyl group, or a cyclohexyl group; each of $R^7$ and $R^8$ independently denotes a hydrogen atom, a methyl group, or a cyclohexyl group; and m denotes 0 or 1.

2. The composition according to claim 1, wherein a cyclic structure comprised in the polyhydroxyl compound is only aromatic carbon rings.

3. The composition according to claim 1, wherein the average molecular weight of the isocyanate compound ranges from 500 to 15,000 as a weight average molecular weight of a dibutylamine adduct of the isocyanate compound that has been dibutylaminated with dibutylamine.

4. The composition according to claim 1, wherein the isocyanate compound is a reaction product of the polyhydroxyl compound and the polyisocyanate, with the number of moles of the polyisocyanate being 0.8 to 1.5-fold the number of moles of hydroxyl groups comprised in the polyhydroxyl compound.

5. The composition according to claim 1, which further comprises binder.

6. The composition according to claim 1, which further comprises binder and ferromagnetic powder.

7. The composition according to claim 6, wherein a cyclic structure comprised in the polyhydroxyl compound is only aromatic carbon rings.

8. A magnetic recording medium, which comprises a magnetic layer on a nonmagnetic support and the magnetic layer is a layer formed by heating the composition according to claim 7.

9. The composition according to claim 6, wherein an average particle size of the ferromagnetic powder ranges from 10 nm to 50 nm.

10. A magnetic recording medium, which comprises a magnetic layer on a nonmagnetic support and the magnetic layer is a layer formed by heating the composition according to claim 9.

11. A magnetic recording medium, which comprises a magnetic layer on a nonmagnetic support and the magnetic layer is a layer formed by heating the composition according to claim 6.

* * * * *